US00PP29550P2

(12) United States Plant Patent
Hansen

(10) Patent No.: US PP29,550 P2
(45) Date of Patent: Jul. 24, 2018

(54) ***SALVIA* PLANT NAMED 'PRETTY IN PINK'**

(50) Latin Name: *Salvia pratensis*
Varietal Denomination: Pretty in Pink

(71) Applicant: Hans A. Hansen, Zeeland, MI (US)

(72) Inventor: Hans A. Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 15/731,782

(22) Filed: Jul. 31, 2017

(51) Int. Cl.
*A01H 5/02* (2018.01)

(52) U.S. Cl.
USPC ..... Plt./475

(58) Field of Classification Search
USPC ..... Plt./475
See application file for complete search history.

*Primary Examiner* — Annette H Para

(57) ABSTRACT

The new and distinct cultivar of perennial *Salvia* plant named 'Pretty in Pink' characterized by its very large deep purplish pink flowers from deep purplish-red buds, densely arranged in verticils. The new plant has a compact habit with stiff, upright, heavily-branched stems showing slight dark greyed-purple tinting and persistent calyxes of similar dark greyed-purple tinting, a strong vigorous growth rate and gray-green foliage.

1 Drawing Sheet

Botanical denomination: *Salvia pratensis.*
Cultivar designation: 'Pretty in Pink'.

BACKGROUND OF THE INVENTION

The present invention relates to a new and distinct cultivar of ornamental sage plant hereinafter referred to by the cultivar name *Salvia* 'Pretty in Pink' or as the new plant. The new plant was selected as a single seedling from an open pollination in late spring of 2013 with 'Pink Dawn' U.S. Plant Pat. No. 26,343 as the female or seed parent and the male parent is unknown but may have been any sage from a large number of other hybrids and selected cultivars within the breeding area of a wholesale perennial nursery in Zeeland, Mich., USA. The new plant was initially evaluated in the summer of 2014 and assigned the breeder code 13-10-1 through the trial process.

The new *Salvia* was further evaluated and asexually propagated by basal cuttings taken at the same nursery in Zeeland, Mich., USA in 2014. Evaluation of these and further cutting grown plants shows that *Salvia* 'Pretty in Pink' continues to be stable and produce true to type plants in successive generations of asexual propagation.

No plants of *Salvia* 'Pretty in Pink' have been sold, in this country or anywhere in the world, prior to the filing of this application, nor has any disclosure of the new plant been made prior to the filing of this application with the exception of that which may have been disclosed within one year of the filing of this application and was either derived directly or indirectly from the inventor.

SUMMARY OF THE INVENTION

Plants of *Salvia* 'Pretty in Pink' have not been observed under all possible environmental conditions. The phenotype may vary somewhat with variations in environment such as temperature, nutrition and light intensity without, however, any variance in genotype.

*Salvia* 'Pretty in Pink' can be closely compared to *Salvia* 'Sweet 16' U.S. Plant Pat. No. 24,312 and *Salvia* 'Pink Dawn' U.S. Plant Pat. No. 26,343. 'Sweet 16' has flowers that are a stronger reddish purple than the new plant. *Salvia* 'Pretty in Pink' can also be compared to *Salvia* 'Pink Dawn' U.S. Plant Pat. No. 26,343, *Salvia* 'Eveline' U.S. Plant Pat. No. 14,905, 'Pink Friesland' U.S. Plant Pat. No. 18,152 and 'Sweet 16' U.S. Plant Pat. No. 24,312. *Salvia* 'Eveline' is slightly taller and has flowers of a lighter purplish pink. The stems and calyxes of 'Pink Dawn' are much darker pigmented with greyed-purple than the new plant, the flowers are darker, deep, purplish pink and the habit is smaller than the new plant. 'Pink Friesland' has a shorter habit and smaller flowers of a stronger purplish red than the new plant. The new plant can also be compared to *Salvia* 'Endless Love' U.S. Plant Pat. No. 21,707 which has a *Salvia verticillata* background and flowers on whorled scapes that are more purple and less pink and smaller in size than the new plant.

The following characteristics in combination distinguish *Saliva* 'Pretty in Pink' as a new and distinct cultivar from all other cultivars known to the inventor:

1. Very large deep purplish pink flowers densely arranged in verticils;
2. Stiff, upright, heavily-branched stems with slight dark greyed-purple tinting;
3. Deep purplish-red flower buds;
4. Compact, rounded, strong, vigorous and winter-hardy habit;
5. Rugose gray-green foliage.

BRIEF DESCRIPTION OF THE DRAWINGS

The photographs of the new plant demonstrate the unique traits and the overall appearance of *Salvia* 'Pretty in Pink'. The colors are as accurate as reasonably possible with color reproductions. Variation in ambient light spectrum, source and direction may cause the appearance of minor variation in color. The plant used in the photographs was a two-year old plant grown in an open, full-sun trial garden at a wholesale perennial nursery in Zeeland, Mich. with supplemental water and fertilizer when needed. Plant growth regulators have been used in greenhouse grown trials only.

DETAILED BOTANICAL DESCRIPTION

Figure 1:
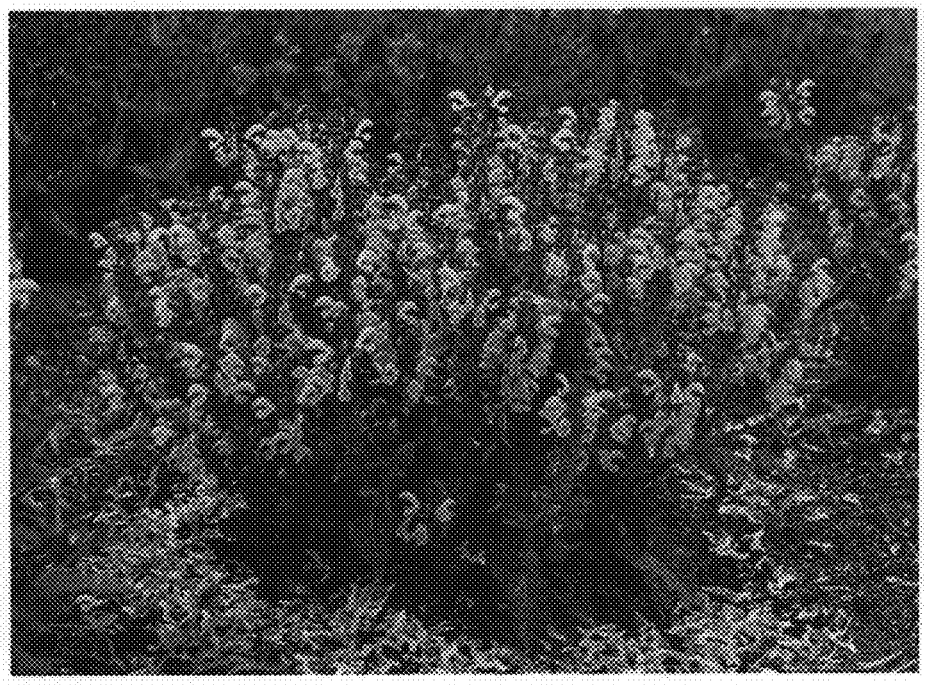
FIG. 1 shows the plant habit in full flower in a landscape.
Figure 2:
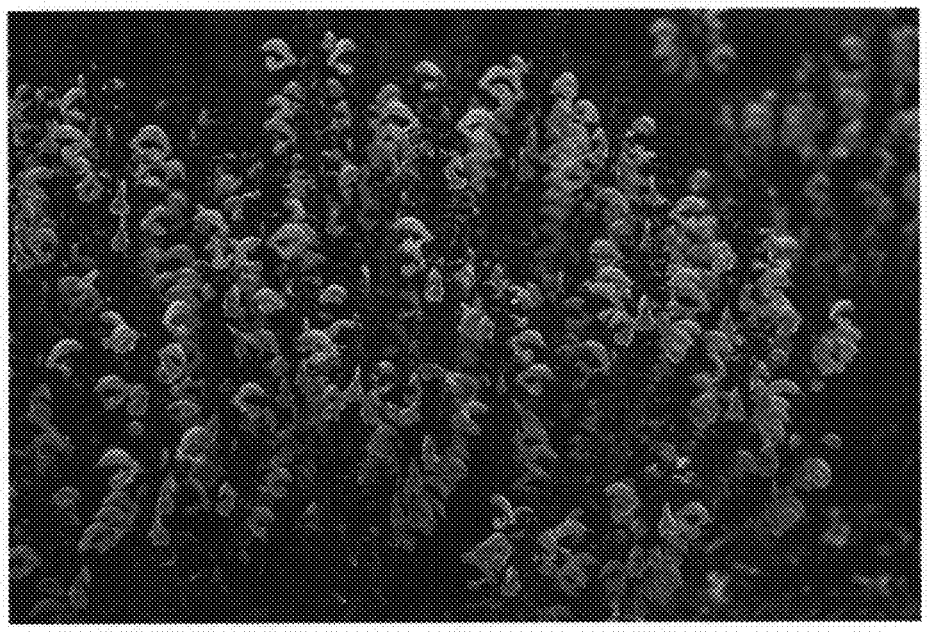
FIG. 2 shows a close-up of the flower scape with the buds, flowers, stems and calyxes.

The following descriptions and color references except where common dictionary terms are used are based on the 2015 edition of The Royal Horticultural Society Colour Chart. *Salvia* 'Pretty in Pink' has not been observed under all possible environments. The phenotype may vary slightly with different growing environments such as temperature, light, fertility, soil pH, moisture and plant maturity levels, but without any change in the genotype. The following observations and size descriptions are based on two-year old plants growing in an outdoor full-sun trial garden at a wholesale perennial nursery in Zeeland, Mich. and greenhouse forced two-year old plants. Plants were given supplemental water and fertilizer and plant growth regulators were used for the greenhouse trials only.

Botanical classification: *Salvia pratensis* (Linnaeus);

Parentage: Female or seed parent 'Pink Dawn'; unknown male or pollen parent;

Plant habit: Winter-hardy herbaceous perennial; multi-stemmed, compact, rounded, with mostly basal foliage, and flowers in several tightly arranged verticils on branched upright racemes displayed above foliage; in flower with panicles about 60 cm tall and about 65 cm wide at the fullest point; foliage extends up the stems about 28 cm and 52 cm wide below foliage;

Propagation: By basal vegetative shoot cuttings; time to produce a rooted stems about two weeks;

Growth rate: Rapid, vigorous, finishing in a 65 mm container in about 7 weeks from rooted cutting, and from 65 mm container to flowering 3.8 liter container in about 8 weeks.

Root description: Fine, well-branched; color dependent on age and soil type, from cream to dark tan in color;

Foliage: Opposite, simple, rugose, lanceolate; margin crenulate; glabrous and matte abaxial and adaxial surfaces; acute apex and base cordate to auriculate with lobes frequently overlapping; leaf blades about 16.5 cm long and 8.0 cm across, decreasing in size distally; average about 12.5 cm long and 5.4 cm across; faint sage fragrance;

Foliage color: Adaxial surface between RHS 138A and RHS 138B; abaxial surface nearest RHS 146B;

Venation: Reticulate; impressed on adaxial side and costate on abaxial side; pubescent abaxial, puberulent adaxial;

Vein color: Adaxial midrib variable, nearest RHS 145C in shaded areas and proximally more gray than RHS 185D and more purple than either RHS N187C or RHS N187B with more intense light; adaxial primary and secondary veins nearest RHS 145C toward midrib and gradually darkening to between RHS 138A and RHS 138B; abaxial midrib nearest RHS 145C with blushing nearest RHS N186C concentrated proximally in leaves with more intense light; abaxial primary veins nearest RHS 145C and secondary veins gradually darkening to nearest RHS 146C toward leaf margin;

Petiole: Concavo-convex; pubescent abaxial and along margin, sparsely puberulent adaxial; to about 9.5 cm long and 6.0 mm wide, average 5.5 cm long and 4.0 mm wide at base;

Petiole color: Adaxial and abaxial surfaces nearest 146D with proximally concentrated blushing of RHS N186C;

Flower description: Perfect, bilabiate, verticillate with flowering generally beginning at lower verticils and advancing up the scape, but not all flowers at each verticil opening at the same time giving the effect of a scape being in continuous flower for longer periods; average distance between verticils about 14.0 mm, greater proximally and less distally; with midline projected about 10 degree angle above horizontal and hood petal about 45 degree angle above horizontal; self-cleaning, petals not persistent; flowering beginning late spring for about six weeks and repeating if initial scapes removed;

Flower longevity: About four days on the plant or as cut flower;

Fragrance: None detected under present growing conditions;

Flower buds one to two days prior to anthesis: Shape is rounded on top and slightly concave below, with rounded apex; pubescent; about 11.0 mm long, 5.0 mm tall and 3.0 mm wide;

Bud color: Exposed petals nearest RHS 71A; abaxial calyx nearest RHS 138A with veins and blushing on dorsal portion nearest RHS 187B;

Flowers: Bilabiate corolla with arcuate hooded upper lip and tri-lobed lower lip; about 2.4 cm long, 14.0 mm tall and 8.0 mm wide fused into tube in the proximal 8.0 mm; clustered at verticils with about six flowers per verticil;

Petals: Bilabiate corolla; upper hood petal and flattened side to side vertically, with notched apex and base fused with labium;

Hood (upper) petal: Minutely pubescent outside, glabrous inside; about 20.0 mm long, 10.0 mm tall and 3.0 mm across;

Labium (lower) petal: Consisting of three lobes, two proximal lobes about 3.0 mm long and 3.0 mm wide at base with rounded apex; center lobe emarginate, about 5.0 mm long 7.0 mm wide with a 2.0 mm apical notch in middle; center lobe slightly concaved upwards; total labium about 15.0 mm long, 8.0 mm wide at the widest portion across lobes and 5.0 mm tall;

Petal color: Abaxial and adaxial hood petal nearest RHS N74C; lower labium petal abaxial nearest RHS N75B and adaxial between RHS 77B and RHS 77A; fused basal 2.0 mm inside calyx nearest RHS NN155D;

Androecium: Two, fused with labium, contained within hood petal except when triggered by pollinator;

*Filament*.—Glabrous, fused about 7.0 mm from base of labium petal; curved around inside of hood petal; about 12.0 mm long and less than 0.5 mm diameter with a 2.0 mm trip mechanism at base; color of base nearest RHS 77D, mid-portion lighter than RHS 84D and blend of lighter than RHS 77D and RHS 84D in distal region before stamen.

*Anther*.—Glabrous, oblong, about 3.0 mm long and 1.0 mm diameter; longitudinal, dorsifixed; color nearest RHS N187A.

*Pollen*.—Abundant; globose; less than 0.1 mm circumference; color nearest RHS 12A.

Gynoecium: One, curved around inside of hood petal;

*Style*.—About 24.0 mm long and less than 0.5 mm diameter; color nearest RHS NN155D and darkening distally about 5.0 mm before stigma split to nearest RHS 77A.

*Stigma*.—Bifurcate and curved in the terminal 2.0 mm; apex pointed; color nearest RHS 77A.

*Ovary*.—Superior; color more green than RHS 145A and more yellow than RHS 138B.

Fruit: Nutlet, one to four per flower; rounded, about 1.5 mm diameter; color darker than RHS 200A;

Calyx: Five sepals, three upper and two lower, campanulate, apex acute; fused in basal 4.0 mm; tube about 7.0 mm long and 6.0 mm tall at mouth and 3.0 mm wide; lower set bifurcate in terminal 2.5 mm; upper set of trifurcate in distal 1.0 mm;

Calyx color: Variable with light intensity, abaxial bases and regions in little direct sunlight nearest RHS 145A with veins of nearest RHS 138A, abaxial regions receiving more intense light developing tinting nearest RHS 187A to a blend of RHS N187 and RHS 187A; adaxial between RHS 146D and RHS 146C with darker veins of RHS 137A toward apex;

Bracts: Each verticil subtended by two opposite nearly cordate bracts; apex acuminate, base truncate, margin entire and ciliolate; coarsely wavy to bent downward toward apex; margin minutely pubescent, and glabrous above and below; bract size up to 12.0 mm long and 8.0 mm wide, decreasing distally;

Bract color: Variable with light intensity, in less light abaxial and adaxial surfaces nearest RHS 138A with midrib and base nearest RHS 145C; color with more intense light between RHS N186C and RHS N186C on both surfaces;

Peduncles: Raceme; quadrangular in base cross section; about 20 per plant; strong; upright; to about 60 cm tall and 5.0 mm across; puberulent to glandular; branches in lower two to four nodes, upright at 50 degrees above horizontal or greater; branches to about 24.0 cm long and 3.0 mm across; average internode distance about 5.0 cm;

Peduncle color: Between RHS 138A and RHS 138B;

Pedicels: Cylindrical; puberulent to glandular; about 1.5 mm long and 0.5 mm diameter; puberulent to glandular; nearly horizontal at flower anthesis;

Pedicel color: Variable with light intensity, ventral portion between RHS 146C and RHS 146D with lower light exposure; nearest RHS N187A in dorsal portions with intense light;

Disease and pest resistance: Plants of *Salvia* 'Pretty in Pink' perform best with adequate moisture and good drainage and are hardy from USDA zone 3 to 8. Resistant to diseases and pests beyond that common to *Salvia* has not been noted.

It is claimed:

1. The new and distinct perennial *Salvia* plant named 'Pretty in Pink' as herein described and illustrated useful for landscaping as a specimen plant, en masse or as a cut flower.

* * * * *